(12) United States Patent
Wang

(10) Patent No.: US 12,178,773 B1
(45) Date of Patent: Dec. 31, 2024

(54) MASSAGER

(71) Applicants: Dongguan Mimao Electronic Technology Co., Ltd., Guangdong (CN); Shenzhen Zhonghongtian Technology Co., Ltd., Shenzhen (CN); Junpeng Wu, Shenzhen (CN)

(72) Inventor: Qinling Wang, Guangdong (CN)

(73) Assignees: Dongguan Mimao Electronic Technology Co., Ltd., Dongguan (CN); Shenzhen Zhonghongtian Technology Co., Ltd., Shenzhen (CN); Jungpeng Wu, Shenzhen (CN)

( * ) Notice: Subject to any disclaimer, the term of this patent is extended or adjusted under 35 U.S.C. 154(b) by 0 days.

(21) Appl. No.: 18/644,172

(22) Filed: Apr. 24, 2024

(30) Foreign Application Priority Data

Apr. 15, 2024 (CN) .......................... 202420778432.4

(51) Int. Cl.
*A61H 19/00* (2006.01)
*A61F 5/41* (2006.01)
*A61H 23/02* (2006.01)

(52) U.S. Cl.
CPC ............... *A61H 19/34* (2013.01); *A61F 5/41* (2013.01); *A61H 19/44* (2013.01); *A61H 19/50* (2013.01); *A61H 23/0254* (2013.01); *A61F 2005/417* (2013.01); *A61H 2201/165* (2013.01)

(58) Field of Classification Search
CPC ........ A61H 19/00; A61H 19/30; A61H 19/32; A61H 19/34; A61H 19/44; A61H 19/50
See application file for complete search history.

(56) References Cited

U.S. PATENT DOCUMENTS

| | | | |
|---|---|---|---|
| 6,056,705 A * | 5/2000 | Stigar-Brown | A61H 19/34 601/84 |
| 6,991,600 B1 * | 1/2006 | Wang | A61H 19/50 600/38 |
| 2005/0124853 A1 * | 6/2005 | Norma | A61H 19/50 600/38 |
| 2015/0182413 A1 * | 7/2015 | Guang | A61H 23/0263 601/46 |
| 2016/0051438 A1 * | 2/2016 | Hahr | A61H 23/0263 601/72 |

* cited by examiner

*Primary Examiner* — Samuel G Gilbert
(74) *Attorney, Agent, or Firm* — Andrew C. Cheng

(57) ABSTRACT

A massager includes a clamping part, a driving mechanism and a positioning portion. The clamping part includes a first engagement portion and a second engagement portion. The first engagement portion and the second engagement portion are opposite to each other and made of a flexible material, with a cavity defined between the first engagement portion and the second engagement portion. The driving mechanism includes at least one swing arm which is disposed in at least one of the first engagement portion and the second engagement portion for driving the at least one of the first engagement portion and the second engagement portion to move toward or away from the other. The positioning portion includes at least one ring or an elongated stick.

20 Claims, 9 Drawing Sheets

MASSAGER

CROSS-REFERENCE TO RELATED APPLICATIONS

The present application claims priority of Chinese Patent Application No. 202420778432.4, filed on Apr. 15, 2024, the entire contents of which are hereby incorporated by reference.

TECHNICAL FIELD

Embodiments of the present invention relate to sex aids, in particular to a massager having a clamping part and at least one ring or an elongated stick.

DESCRIPTION OF THE PRIOR ART

Massagers, as a type of health care device, have been developed in various shapes, sizes, and functions to provide massage and/or stimulation to various parts of the human body. However, some existing massagers are easy to fall off during use, resulting in bad user experiences.

SUMMARY

Embodiments include a massager including a clamping part, a driving mechanism and a positioning portion. The clamping part includes a first engagement portion and a second engagement portion. The first engagement portion and the second engagement portion are opposite to each other and made of a flexible material, with a cavity defined between the first engagement portion and the second engagement portion. The driving mechanism includes at least one swing arm which is disposed in at least one of the first engagement portion and the second engagement portion for driving the at least one of the first engagement portion and the second engagement portion to move toward or away from the other. The positioning portion includes at least one ring or an elongated stick.

In one aspect, the massager can provide clamping massage and stimulation to the part of the human body, especially to the C spot (clitoris) of the woman, through the first and second engagement portions, thereby improving the sex life of the woman. In another aspect, the massager can be positioned during use through the positioning portion (at least one ring or an elongated stick), preventing the massager from falling off during use and providing a good user experience. In particular, when the massager includes the at least one ring, the at least one ring can be disposed around the penis and/or the pair of testicles of the man to enhance the erection. When the massager includes the elongated stick, the elongated stick can be inserted into the vagina or the rectum of the woman/man, to stimulate the vagina or the rectum, further improving the sex life of the woman/man.

BRIEF DESCRIPTION OF DRAWINGS

The accompanying drawings, which are incorporated in and constitute a part of this specification, illustrate several embodiments of the present disclosure and together with the description, serve to explain the principles of the present disclosure.

DESCRIPTION OF EMBODIMENTS

Reference throughout this specification to "one embodiment", "an embodiment", "some embodiments", "embodiments", or similar language means that a particular feature, structure, or characteristic described in connection with the embodiment is included in at least one embodiment of the present disclosure. Thus, appearances of the phrases "in one embodiment", "in an embodiment", "in some embodiments", "in embodiments" and similar language throughout this specification may, but do not necessarily, all refer to the same embodiment.

The terminology used herein is for the purpose of describing particular embodiments only and is not intended to be limiting of this disclosure. As used herein, the singular forms "a", "an", and "the" are intended to include the plural forms as well, unless the context clearly indicates otherwise.

Furthermore, the use of the terms "a", "an", etc., do not denote a limitation of quantity, but rather denote the presence of at least one of the referenced items. It will be further understood that the terms "comprises" and/or "comprising", or "includes" and/or "including", or "has" and/or "having", when used in this specification, specify the presence of stated features, regions, integers, steps, operations, elements, and/or components, but do not preclude the presence or addition of one or more other features, regions, integers, steps, operations, elements, components, and/or groups thereof.

For the purposes of disclosure, the word "substantially" is defined as "for the most part", it means "to a great extent", but having some room for some minor variation.

Moreover, the described features, structures, or characteristics of the disclosure may be combined in any suitable manner in one or more embodiments. Features, structures, or characteristics of one embodiment can be mixed and matched with features, structures, or characteristics of another embodiment. It will be apparent to those skilled in the art that various modifications and variations can be made to the present disclosure without departing from the spirit and scope and purpose of the disclosure. Thus, it is intended that the present disclosure cover the modifications and variations of this disclosure provided they come within the scope of the appended claims and their equivalents. Reference will now be made in detail to the preferred embodiments of the disclosure.

Figure 1:
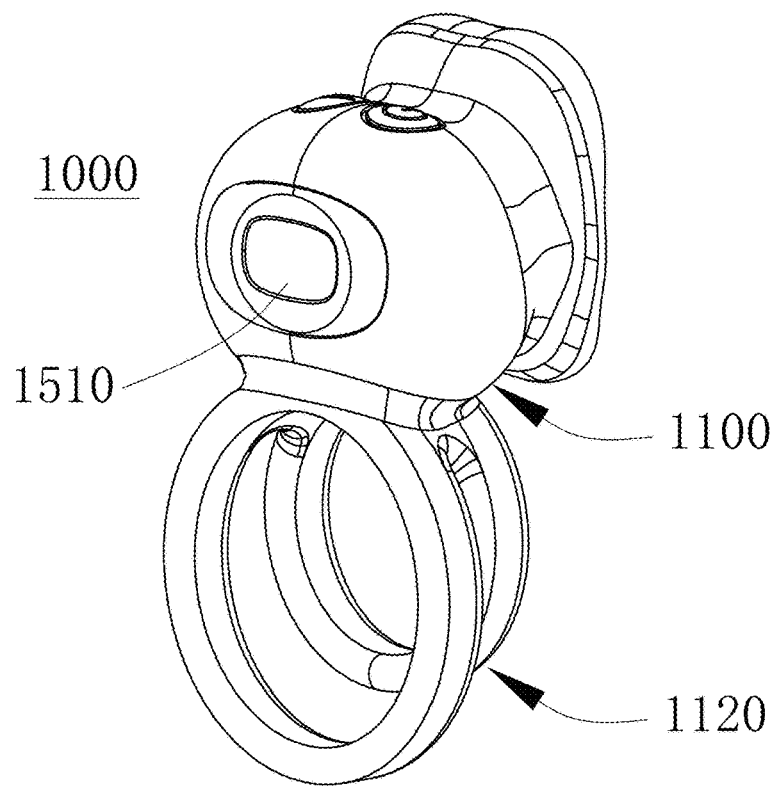
FIG. 1 is a perspective view of a massager according to a first embodiment of the present disclosure.
Figure 2:
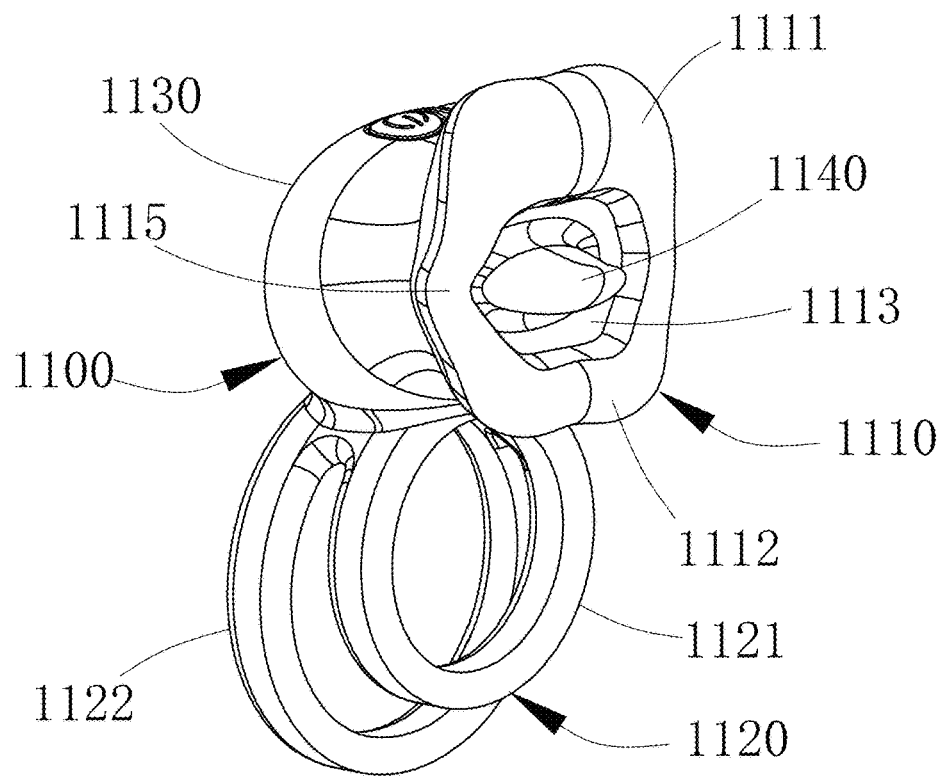
FIG. 2 is another perspective view of the massager shown in FIG. 1.
Figure 3:
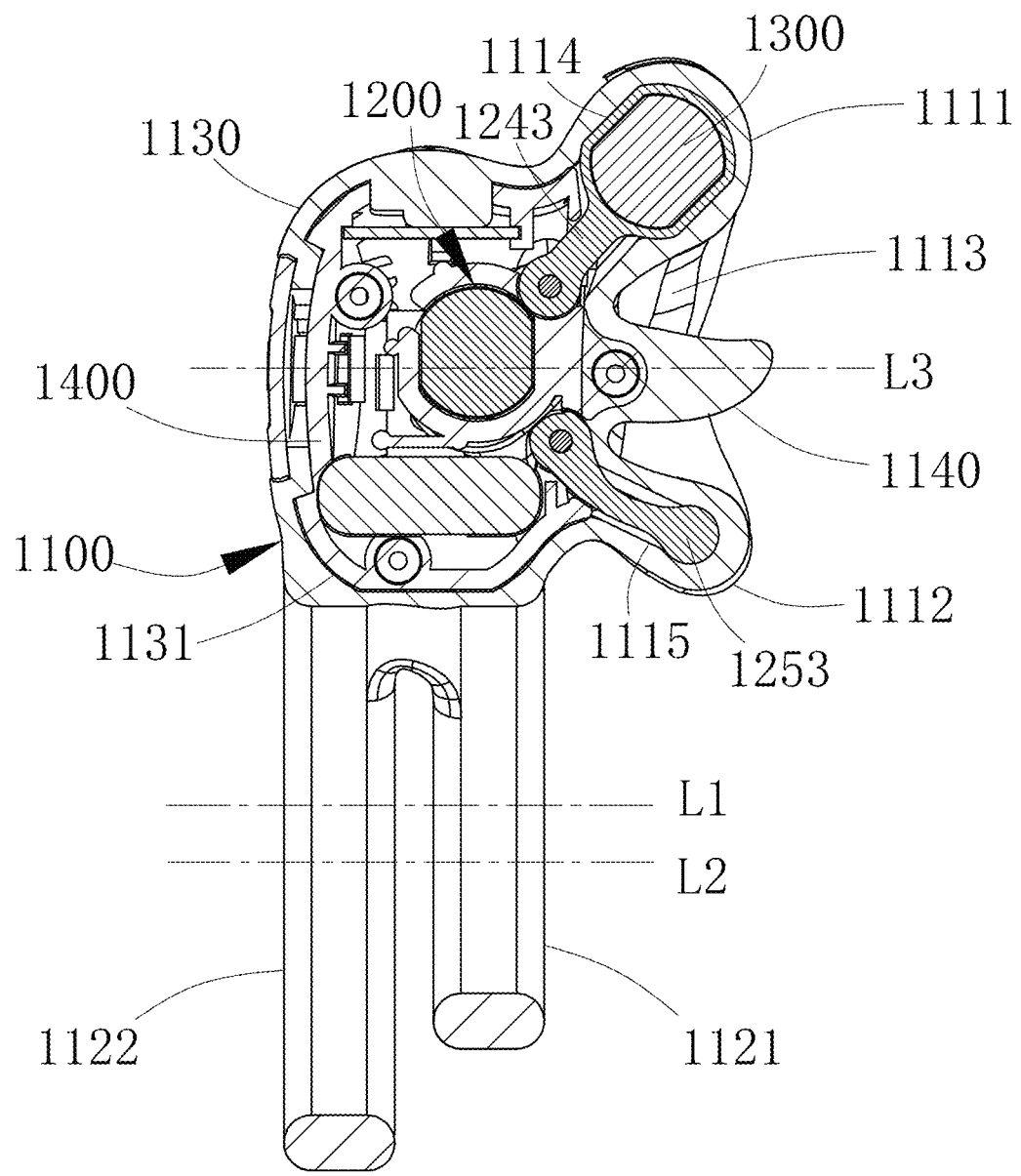
FIG. 3 is a cross-sectional view of the massager shown in FIG. 1.

Referring to FIGS. 1 to 3, a massager 1000 according to a first embodiment of the present disclosure includes an outer housing 1100 and a driving mechanism 1200 accommodated in the outer housing 1100. The outer housing 1100 includes a clamping part 1110 and a positioning portion 1120. The clamping part 1110 includes a first engagement portion 1111 and a second engagement portion 1112 that are opposite to each other. There is a cavity 1113 between the first engagement portion 1111 and the second engagement portion 1112. The first engagement portion 1111 and the second engagement portion 1112 are made of a flexible material. In this embodiment, the positioning portion 1120 includes a first ring 1121 and a second ring 1122. The driving mechanism 1200 includes at least one swing arm 1210. The at least one swing arm 1210 is disposed in at least one of the first engagement portion 1111 and the second engagement portion 1112 and is configured to drive the at least one of the first engagement portion 1111 and the second engagement portion 1112 to move toward or away from the other.

When the massager 1000 according to this embodiment is in use, it can not only provide clamping massage and stimulation to the part of the human body, especially to the C spot (clitoris) of the woman, by driving the at least one of the first engagement portion 1111 and the second engagement portion 1112 to move toward or away from the other, simulating a mouth of a human, through the at least one swing arm 1210 of the driving mechanism 1200, but can also be positioned through the first ring 1121 and the second ring 1122, preventing the massager 1000 from falling off during use and providing a good user experience. In particular, in this embodiment, the first ring 1121 and the second ring 1122 can be disposed around the penis and the pair of testicles of the man, respectively, to enhance the erection. That is, by using the massager 1000 according to this embodiment, the C spot (clitoris) of the woman, the penis and the testicles of the man can be stimulated simultaneously, thereby improving the sex life of both the man and the woman.

Figure 4:
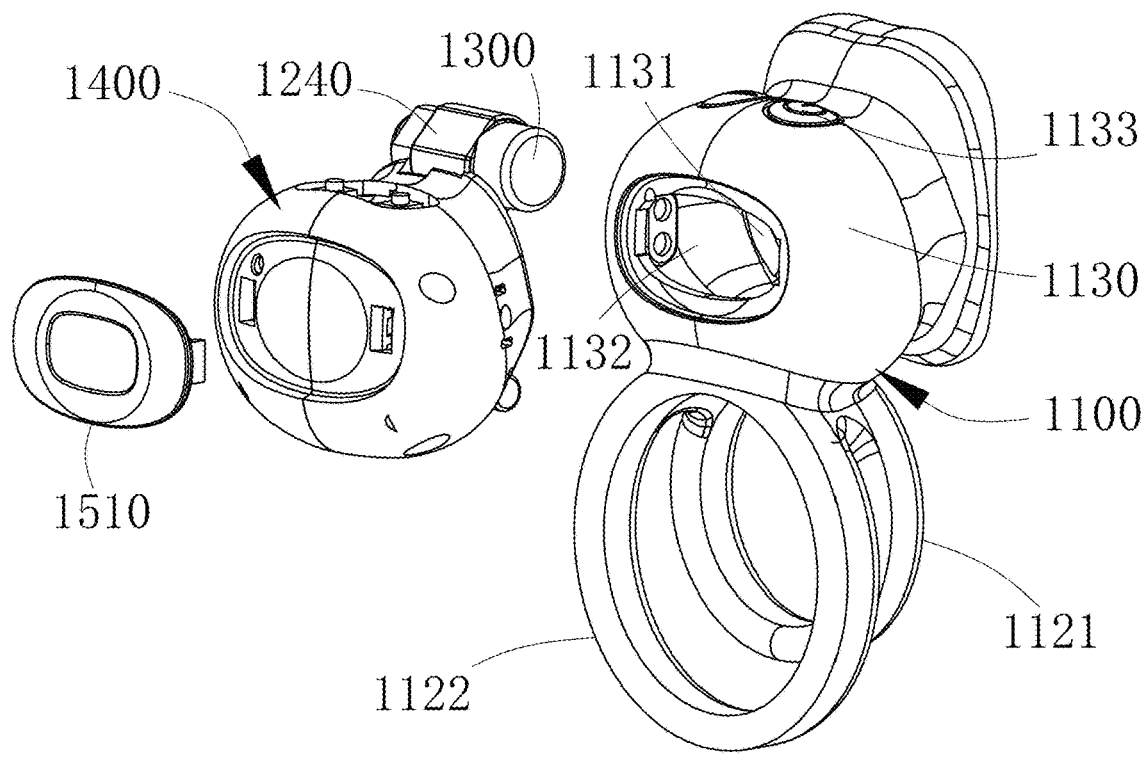
FIG. 4 is an exploded view of the massager shown in FIG. 1.

Specifically, referring to FIGS. 2 to 4, in this embodiment, in addition to the clamping part 1110 and the positioning portion 1120, the outer housing 1100 further includes a main body 1130 for connecting the clamping part 1110 and the positioning portion 1120. The main body 1130 is also preferably made of a flexible material. In this embodiment, the main body 1130 is generally elliptical and has a main chamber 1131 therein.

In this embodiment, the first engagement portion 1111 and the second engagement portion 1112 are provided on the front side of the main body 1130 and arranged at an angle relative to one another. The first engagement portion 1111 and the second engagement portion 1112 respectively have a first accommodation chamber 1114 and a second accommodation chamber 1115. The first accommodation chamber 1114 and the second accommodation chamber 1115 are both communicated with the main chamber 1131. Preferably, two ends of the first engagement portion 1111 are respectively connected to two ends of the second engagement portion 1112 to form two connection portions 1115. Each connection portion 1115 is V-shaped, and the first engagement portion 1111 and the second engagement portion 1112 enclose the cavity 1113.

Optionally, the outer housing 1100 further includes a protrusion 1140, and the protrusion 1140 is also made of a flexible material. The protrusion 1140 is located in the cavity 1113 and between the first engagement portion 1111 and the second engagement portion 1112. In use, the protrusion 1140, like a tongue of a human, can also stimulate the C spot (clitoris) of the woman.

Preferably, the massager 1000 further includes at least one vibration member 1300 provided in at least one of the first engagement portion 1111, the second engagement portion 1112 and the protrusion 1140. As shown in the figure, in this embodiment, the massager 1000 includes a vibration member 1300 disposed in the first engagement portion 1111. Therefore, when the first engagement portion 1111 and the second engagement portion 1112 stimulate the C spot (clitoris) of the woman, the first engagement portion 1111 also vibrates, which improves the massage and stimulation effect. The vibration member 1300 is preferably a vibration motor. It can be appreciated that in other embodiments, the vibration member 1300 can be provided in the second engagement portion 1112 or the protrusion 1140. Alternatively, any two of the first engagement portion 1111, the second engagement portion 1112 and the protrusion 1140 can be provided with vibration members 1300. Alternatively, each of the first engagement portion 1111, the second engagement portion 1112 and the protrusion 1140 can be provided with a vibration member 1300.

In this embodiment, the first ring 1121 and the second ring 1122 are provided on the lower side of the main body 1130. The central axis L1 of the first ring 1121 and the central axis L2 of the second ring 1122 are parallel to each other and parallel to the central axis L3 of the cavity 1113. In this embodiment, the first ring 1121 and the second ring 1122 are both formed as complete rings. That is, both the first ring 1121 and the second ring 1122 extend by 360°. The inner diameter of the first ring 1121 is smaller than the inner diameter of the second ring 1122. Optionally, the inner diameter of the first ring 1121 or the inner diameter of the second ring 1122 is in the range of 5-100 mm.

Alternatively, in other embodiments, the positioning portion 1120 can include more or less rings, such as one, three, four rings, or the like. In other embodiments, the ring is not limited to forming as a complete ring. For example, it can be formed into a semicircle or an arc, as long as it has a through hole through which the penis or the testicles of the man can pass. In addition, the ring is not limited to being arranged so that its central axis is parallel to the central axis L3 of the cavity 1113 as shown in the figure. In other embodiments, the central axis of the ring may be perpendicular to or at other angles to the central axis L3 of the cavity 1113. In the case where the positioning portion 1120 includes a plurality of rings, the plurality of rings are not limited to being arranged so that the central axes of the plurality of rings are parallel to each other as shown in the figure, but may be arranged at an angle/angles relative to each other.

Preferably, the outer housing 1100 is formed in one piece made of a flexible material, preferably silicone. That is, the clamping part 1110, the positioning portion 1120, the main portion 1130 and the protrusion 1140 are formed in one piece.

Figure 5:
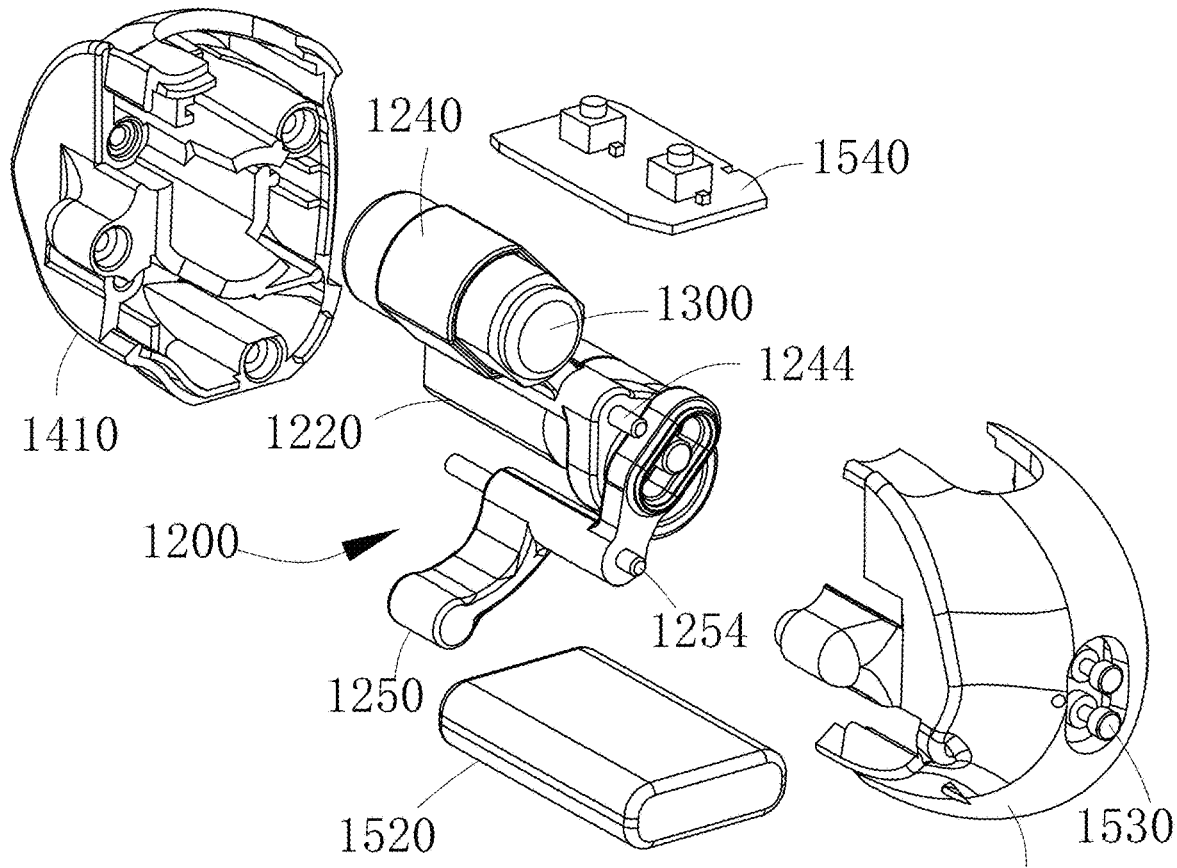
FIG. 5 is an exploded view of an inner housing of the massager shown in FIG. 4.

In order to facilitate the installation of the driving mechanism 1200 and other components of the massager 1000, referring to FIGS. 3 to 5, in this embodiment, the massager 1000 further includes an inner housing 1400 made of a rigid material, for example a rigid plastic. The inner housing 1400 is received in the main chamber 1131 of the outer housing 1100. Optionally, the massager 1000 further includes a cover 1510 that snaps with the inner housing 1400 and covers the opening 1132 of the main chamber 1131. In this embodiment, the inner housing 1400 includes a first housing half 1410 and a second housing half 1420 that are detachably connected with each other. The first housing half 1410 and the second housing half 1420 define a plurality of installation chambers for installing the driving mechanism 1200, a battery 1520 for powering the driving mechanism 1200, a first circuit board 1530 electrically connected to the battery 1520, and a second circuit board 1540 electrically connected to the driving mechanism 1200 for controlling the driving mechanism 1200. The second circuit board 1540 cooperates with a key portion 1133 on the main body 1130 so that the operator can operate the massager 1000.

Figure 6:
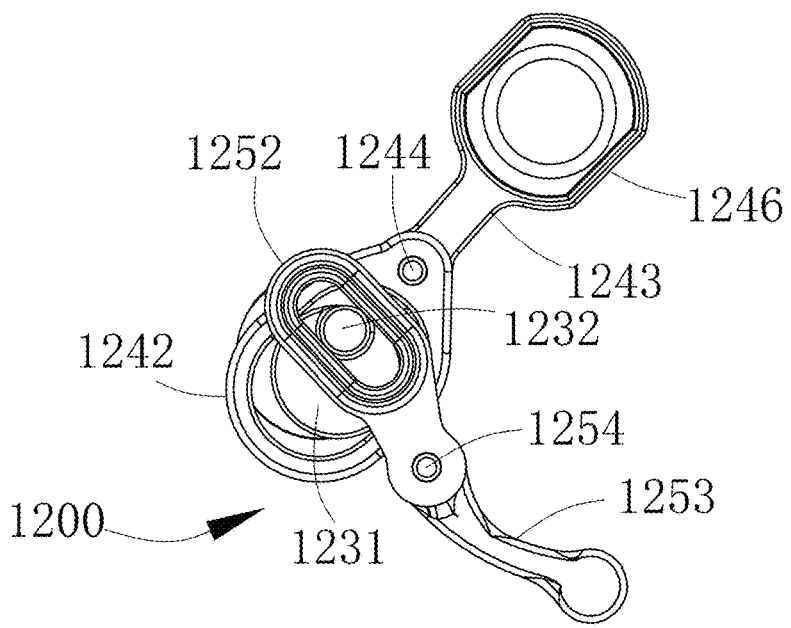
FIG. 6 is a side view of a driving mechanism in the inner housing shown in FIG. 5.
Figure 7:
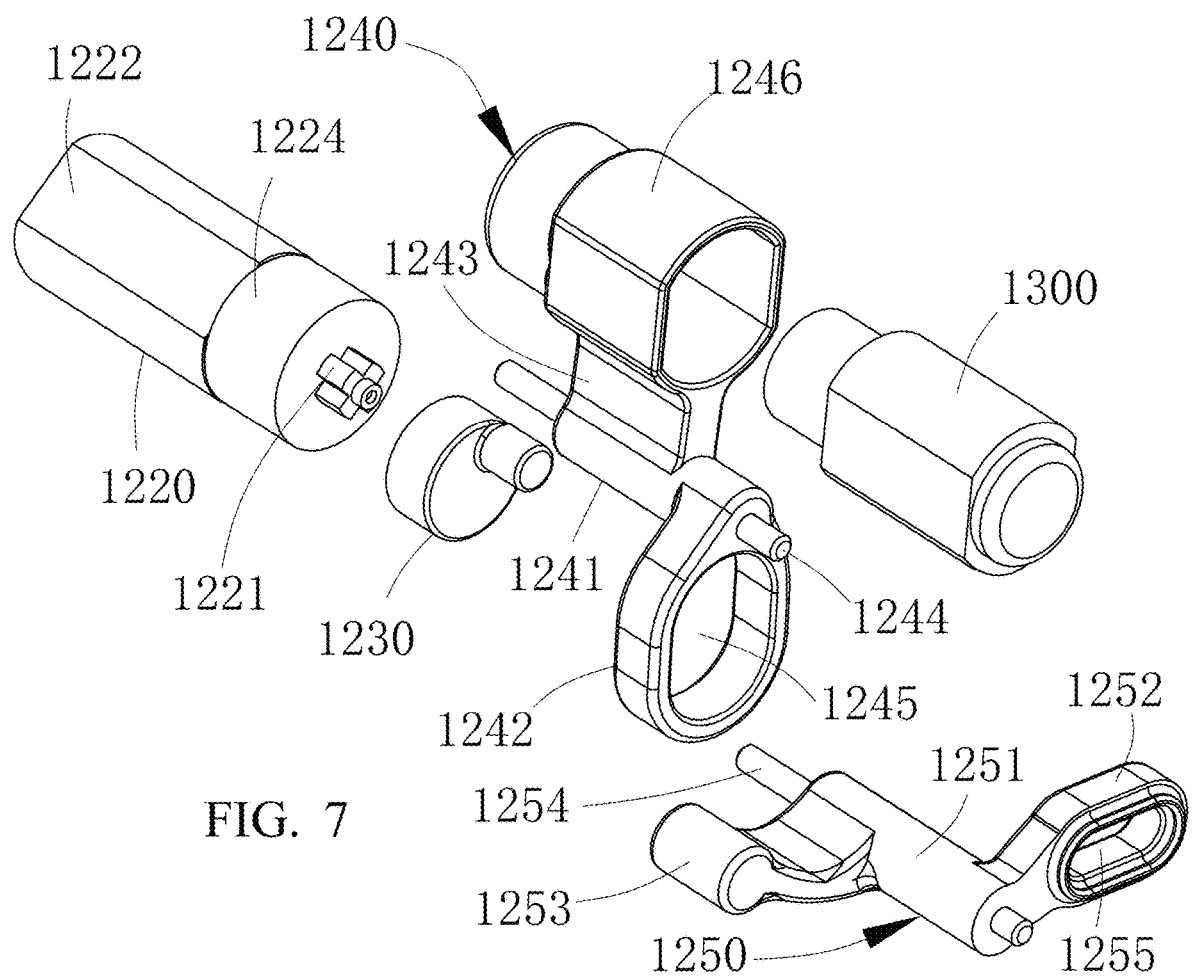
FIG. 7 is an exploded view of the driving mechanism in the inner housing shown in FIG. 5.

Referring to FIGS. 5 to 7, in this embodiment, the driving mechanism 1200 includes a driving source 1220, an eccentric wheel 1230 connected to a driving shaft 1221 of the driving source 1220, and a first swing member 1240 and a second swing member 1250 that are connected to the eccentric wheel 1230. The first swing member 1240 and the second swing member 1250 are arranged at an angle relative to one another.

Figure 8:
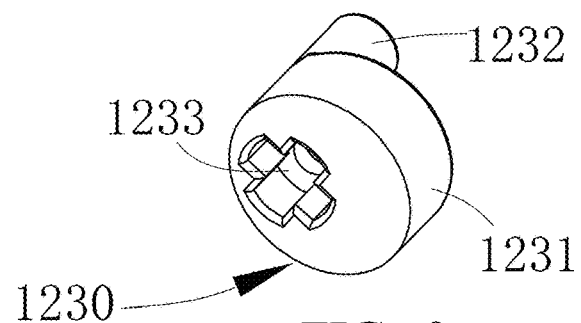
FIG. 8 is a perspective view of an eccentric wheel of the driving mechanism shown in FIG. 7.

As shown in FIG. 8, in this embodiment, the eccentric wheel 1230 includes a first wheel 1231 and a second wheel 1232. An eccentric connection hole 1233 is defined in one side of the first wheel 1231 for connecting with the driving shaft 1221 of the driving source 1220. As shown in the figure, in this embodiment, the connection hole 1233 is a plum blossom-shaped hole. Correspondingly, the driving shaft 1221 is also plum blossom-shaped. Therefore, the driving shaft 1221 of the driving source 1220 and the eccentric wheel 1230 are prevented from rotating relative to each other, so that the eccentric wheel 1230 can rotate synchronously with the driving shaft 1221. The second wheel 1232 is eccentrically located at the other side of the first wheel 1231.

Referring again to FIGS. 6 and 7, in this embodiment, the first swing member 1240 includes a first mounting post 1241, a first collar 1242 and a first swing arm 1243 respectively connected to two sides of the first mounting post 1241. The first mounting post 1241 is rotatably supported in the inner housing 1400 through a first rotation shaft 1244. The first collar 1242 has a first slide groove 1245 so that it can be arranged around the first wheel 1231, and the first wheel 1231 is slidably received in the first slide groove 1245. The first swing arm 1243 extends out of the inner housing 1400 and has a receiving sleeve 1246 for receiving the vibration member 1300.

The second swing member 1250 includes a second mounting post 1251, a second collar 1252 and a second swing arm 1253 respectively connected to two sides of the second mounting post 1251. The second mounting post 1251 is rotatably supported in the inner housing 1400 through a second rotation shaft 1254. The second collar 1252 has a second slide groove 1255 so that it can be arranged around the second wheel 1232, and the second wheel 1232 is slidably received in the second slide groove 1255. The second swing arm 1253 extends out of the inner housing 1400.

In other words, in this embodiment, the at least one swing arm 1210 includes the first swing arm 1243 and the second swing arm 1253. As shown in FIG. 3, the first swing arm 1243 extending out of the inner housing 1400 is received in the first accommodation chamber 1114 of the first engagement portion 1111 and supports the first engagement portion 1111. The second swing arm 1253 extending out of the inner housing 1400 is received in the second accommodation chamber 1115 of the second engagement portion 1112 and supports the second engagement portion 1112. When the driving source 1220 works, the driving shaft 1221 of the driving source 1220 rotates, and the eccentric wheel 1230 is driven to rotate by the driving shaft 1221. The eccentric wheel 1230 drives the first swing member 1240 and the second swing member 1250 to swing around the first rotation shaft 1244 and the second rotation shaft 1254 respectively, so the first swing arm 1243 and the second swing arm 1253 will respectively drive the first engagement portion 1111 and the second engagement portion 1112 to move toward or away from each other simultaneously, thereby realizing clamping massage.

Figure 9:
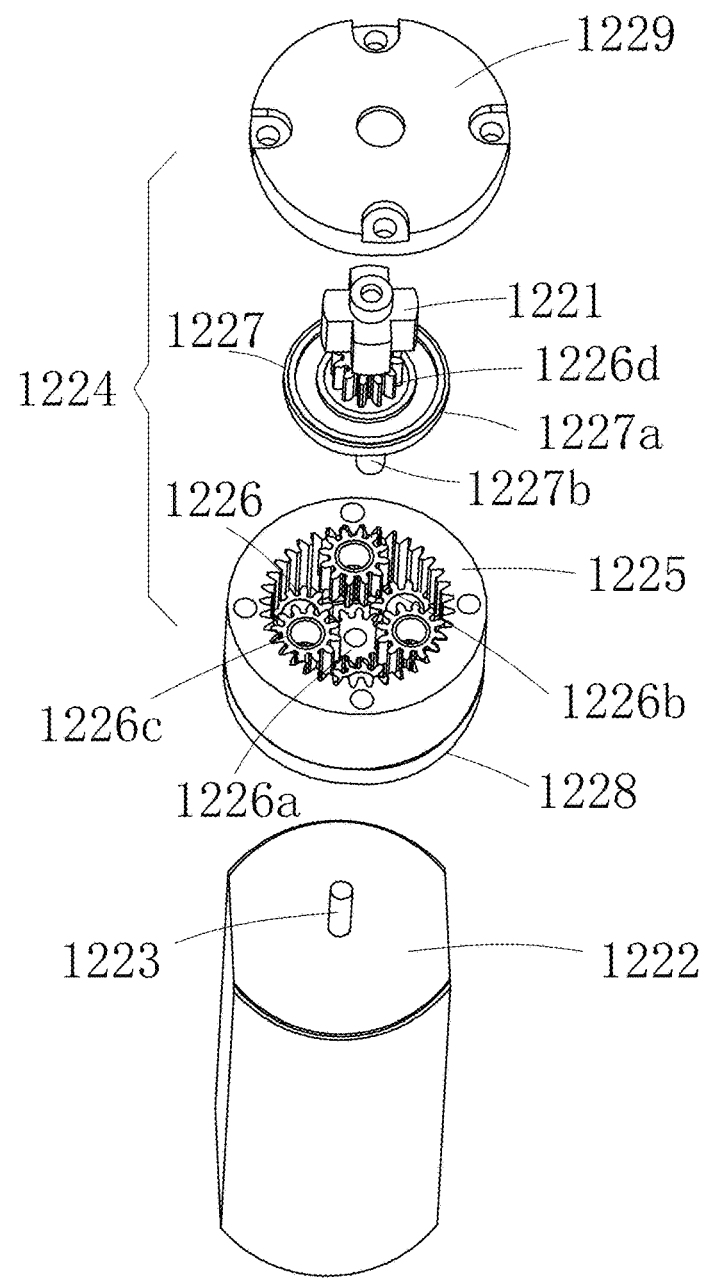
FIG. 9 is an exploded view of a driving source of the driving mechanism shown in FIG. 7.

Referring to FIG. 9, in this embodiment, the driving source 1220 preferably includes a motor 1222 and a reduction gearbox 1224 connected to the output shaft 1223 of the motor 1222. The driving shaft 1221 of the driving source 1220 is provided by the reduction gearbox 1224. Therefore, the rotation speed of the driving shaft 1221 of the driving source 1220 is smaller than the rotation speed of the output shaft 1223 of the motor 1222, and thus the swing frequency of the first swing arm 1243 and the second swing arm 1253 is also small, improving the massage comfort.

As an example, the reduction gearbox 1224 includes an inner gear ring 1225, a plurality of gears 1226 accommodated in the inner gear ring 1225, a rotation frame 1227 that cooperates with the plurality of gears 1226, and a bottom plate 1228 and a top plate 1229 respectively covering two ends the inner gear ring 1225. The plurality of gears 1226 include a first sun gear 1226a close to the base plate 1228 and connected to the output shaft 1223 of the motor 1222, and a plurality of first planetary gears 1226b (here, three first planetary gears 1226) meshed with the first sun gear 1226a and the inner gear ring 1225, a plurality of second planetary gears 1226c (here, three second planetary gears 1226c) meshed with the inner gear ring 1225 and close to the top plate 1229, and a second sun gear 1226d meshed with the plurality of second planetary gears 1226c and close to the top plate 1229.

The rotation frame 1227 includes a partition plate 1227a and a plurality of connection shafts 1227b (here, three connection shafts 1227b) connected to the first side of the partition plate 1227a. The partition plate 1227a is located in the inner gear ring 1225 substantially at the axially middle position to divide the internal space of the inner gear ring 1225 into two layers, wherein the first planetary gears 1226b and the first sun gear 1226a are located on the lower layer close to the bottom plate 1228, with the connection shafts 1227b respectively connected to the corresponding first planetary gears 1226b, and the second planetary gears 1226c and the second sun gear 1226d are located on the upper layer close to the top plate 1229. In this embodiment, the driving shaft 1221 is coaxially connected to the second sun gear 1226d and is located outside the top plate 1229.

The above driving source 1220 is only shown as an example. In other embodiments, the driving source 1220 may use other configurations, which will not be described again here.

Figure 10:
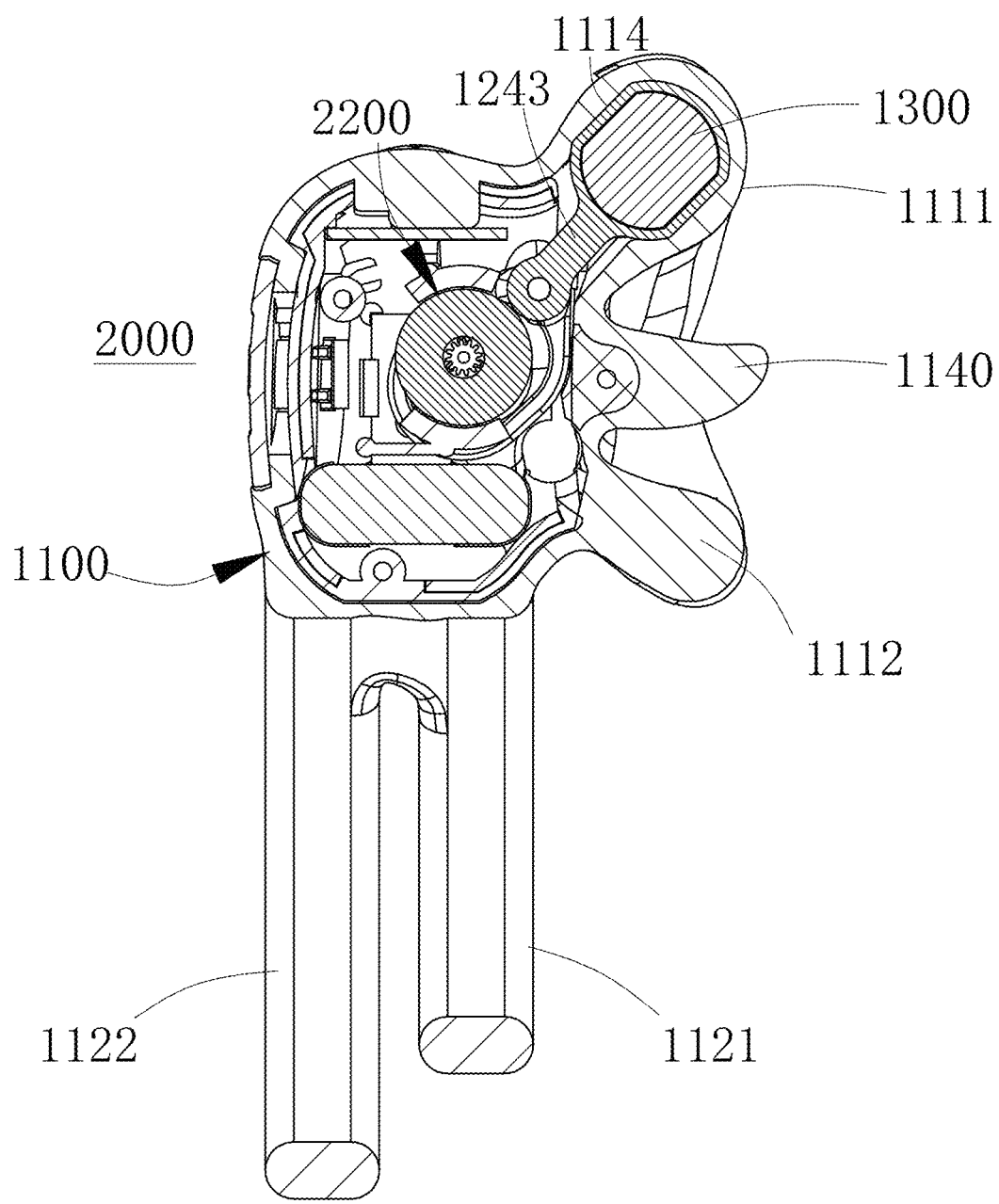
FIG. 10 is a cross-sectional view of a massager according to a second embodiment of the present disclosure.
Figure 11:
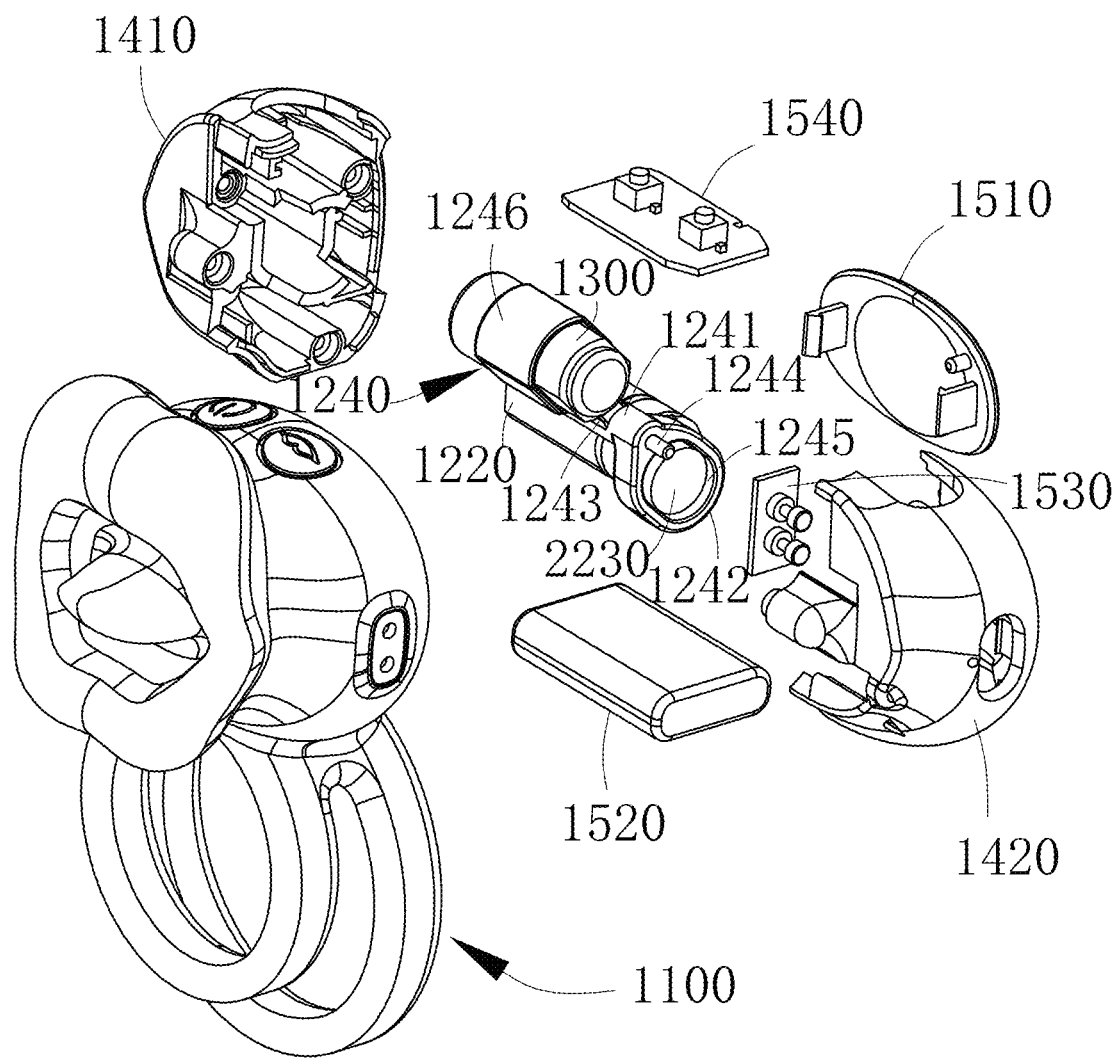
FIG. 11 is an exploded view of the massager shown in FIG. 10.

Referring to FIGS. 10 and 11, the massager 2000 according to a second embodiment of the present disclosure is substantially the same as the massager 1000 according to the first embodiment, and the similarities therebetween will not be repeated here again. The main difference between them is that the driving mechanism 2200 of the massager 2000 according to the second embodiment includes the first swing member 1240 and no longer includes the second swing member 1250. Correspondingly, the eccentric wheel 2230 according to the second embodiment no longer includes the second wheel 1232, but only includes the first wheel 1231.

Similar to the first embodiment, in the second embodiment, the first swing member 1240 also includes the first mounting post 1241, and the first collar 1242 and the first swing arm 1243 respectively connected to two sides of the first mounting post 1241. The first mounting post 1241 is rotatably supported in the inner housing 1400 through the first rotation shaft 1244. The first collar 1242 has the first slide groove 1245 so that it can be arranged around the eccentric wheel 2230, and the eccentric wheel 2230 is slidably received in the first slide groove 1245. The first swing arm 1243 has the receiving sleeve 1246 for receiving the vibration member 1300. The first swing arm 1243 is received in the first accommodation chamber 1114 of the first engagement portion 1111 and supports the first engagement portion 1111. However, in the second embodiment, the second engagement portion 1112 does not have the second accommodation chamber 1115. When the driving source 1220 works, the driving shaft 1221 of the driving source 1220 rotates, and the eccentric wheel 2230 is driven to rotate by the driving shaft 1221. The eccentric wheel 2230 drives the first swing member 1240 to swing around the first rotation shaft 1244, so the first swing arm 1243 will drive the first engagement portion 1111 to move toward or away from the second engagement portion 1112 (the second engagement portion 1112 remains stationary), thereby achieving clamping massage.

In other embodiments, the driving mechanism 2200 may include the second swing member 1250 instead of the first swing member 1240. That is, the first engagement portion 1111 may remain stationary, and the second engagement portion 1112 is driven by the second swing member 1250 to swing toward or away from the first engagement portion 1111, thereby achieving clamping massage.

Figure 12:
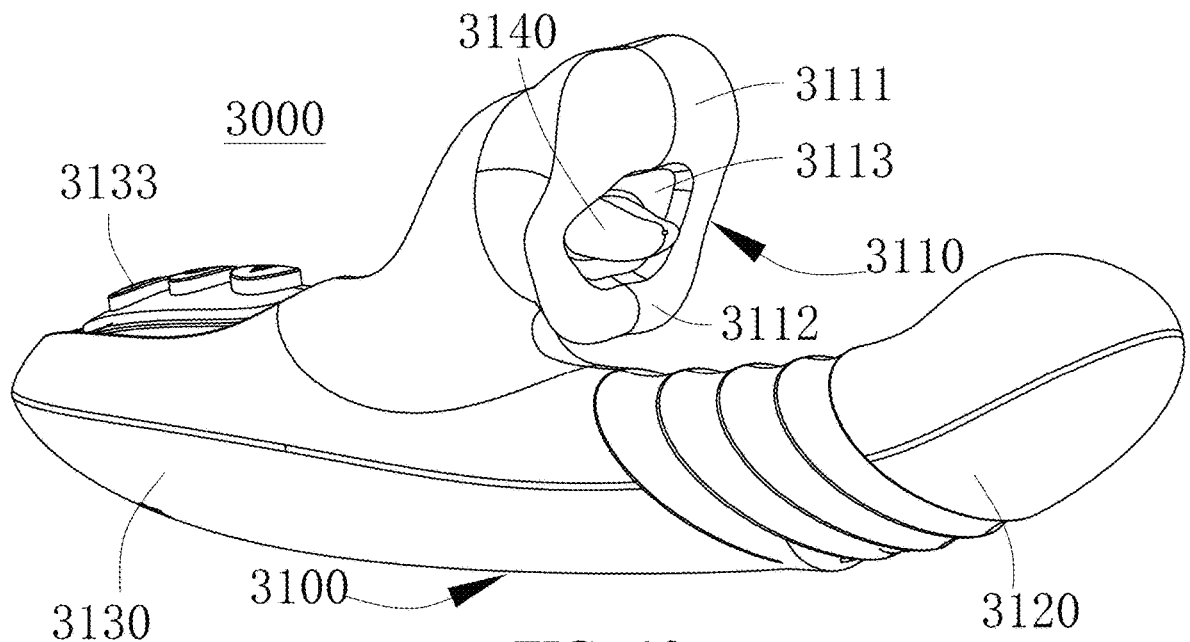
FIG. 12 is a perspective view of the massager according to a third embodiment of the present disclosure.
Figure 13:
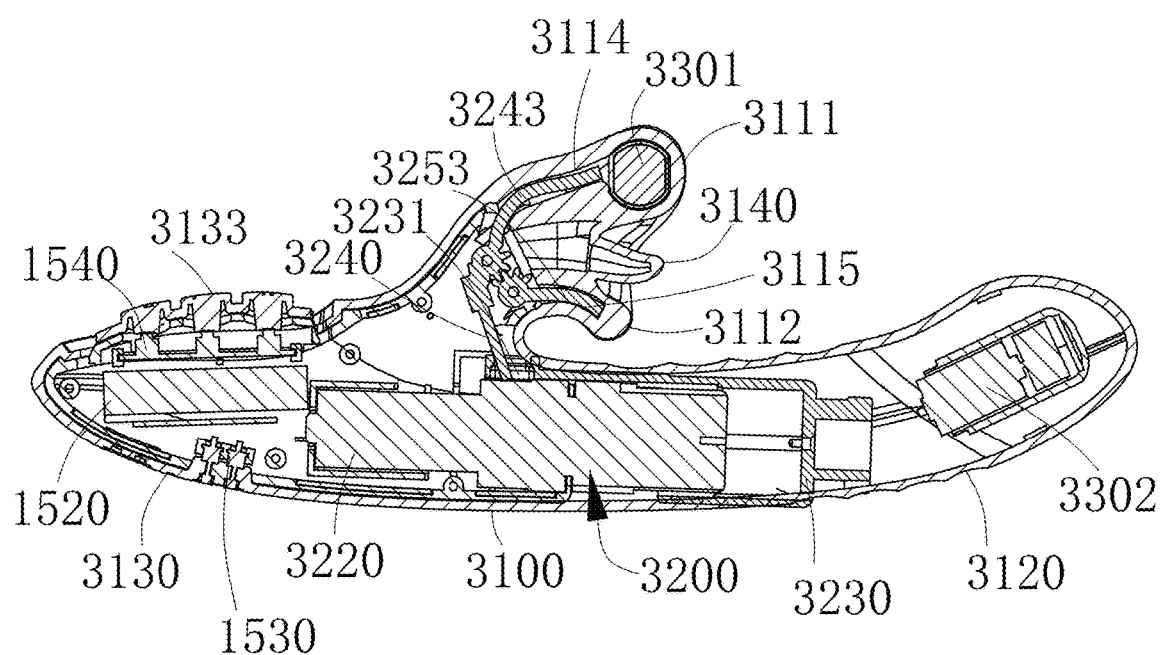
FIG. 13 is a cross-sectional view of the massager shown in FIG. 12.

Referring to FIGS. 12 and 13, similar to the massager 1000 according to the first embodiment, the massager 3000 according to a third embodiment of the present disclosure also includes a clamping part 3110. The clamping part 3110 includes a first engagement portion 3111 and a second engagement portion 3112 that are opposite to each other. There is a cavity 3113 between the first engagement portion 3111 and the second engagement portion 3112, and a tongue-like protrusion 3140 is provided in the cavity 3113. In addition, the driving mechanism 3200 of the massager 3000 according to the third embodiment also includes a first swing arm 3243 and a second swing arm 3253, wherein the first swing arm 3243 is received in a first accommodation chamber 3114 of the first engagement portion 3111 and supports the first engagement portion 3111. The second swing arm 3253 is received in a second accommodation chamber 3115 of the second engagement portion 3112 and supports the second engagement portion 3112. The first swing arm 3243 and the second swing arm 3253 are configured to drive the first engagement portion 3111 and the second engagement portion 3112 to move toward or away from each other simultaneously to achieve clamping massage. However, the specific working principle and structure of the driving mechanism 3200 of the massager 3000 according to the third embodiment are different from those of the driving mechanism 1200 according to the first embodiment, and the positioning portion 3120 of the massager 3000 according to the third embodiment is also different from the positioning portion 1120 according to the first embodiment.

As shown in the figure, the positioning portion 3120 of the massager 3000 according to the third embodiment is an elongated stick. The stick has a length in a range of 2-30 cm. It should be noted that the stick can be straight or slightly curved, and the diameter of the stick can be varied as required. In addition to the clamping part 3110 and the positioning portion 3120, the outer housing 3100 according to the third embodiment further includes a handle portion 3130. In the present embodiment, the handle portion 3130 and the positioning portion 3120 together form an arc-shaped stick. The clamping part 3110 is connected between the handle portion 3130 and the positioning portion 3120 and is arranged at an angle relative to the positioning portion 3120. Specifically, the clamping portion 3110 and the handle portion 3130 are connected to the rear end of the positioning portion 3120, wherein the clamping portion 3110 is arranged at an angle relative to the positioning portion 3120, and the front end of the positioning portion 3120 is a free end. During use, the positioning portion 3120 can be inserted into the vagina or the rectum of woman/man to achieve positioning, preventing the massager 3000 from falling off and providing a good user experience. Further, the massager 3000 according to the third embodiment cannot only provide clamping massager through the clamping part 3110, but can also massage and stimulate the vagina or the rectum of woman/man through the stick-like positioning portion 3120, to improve the sex life of the man/woman.

Figure 14:
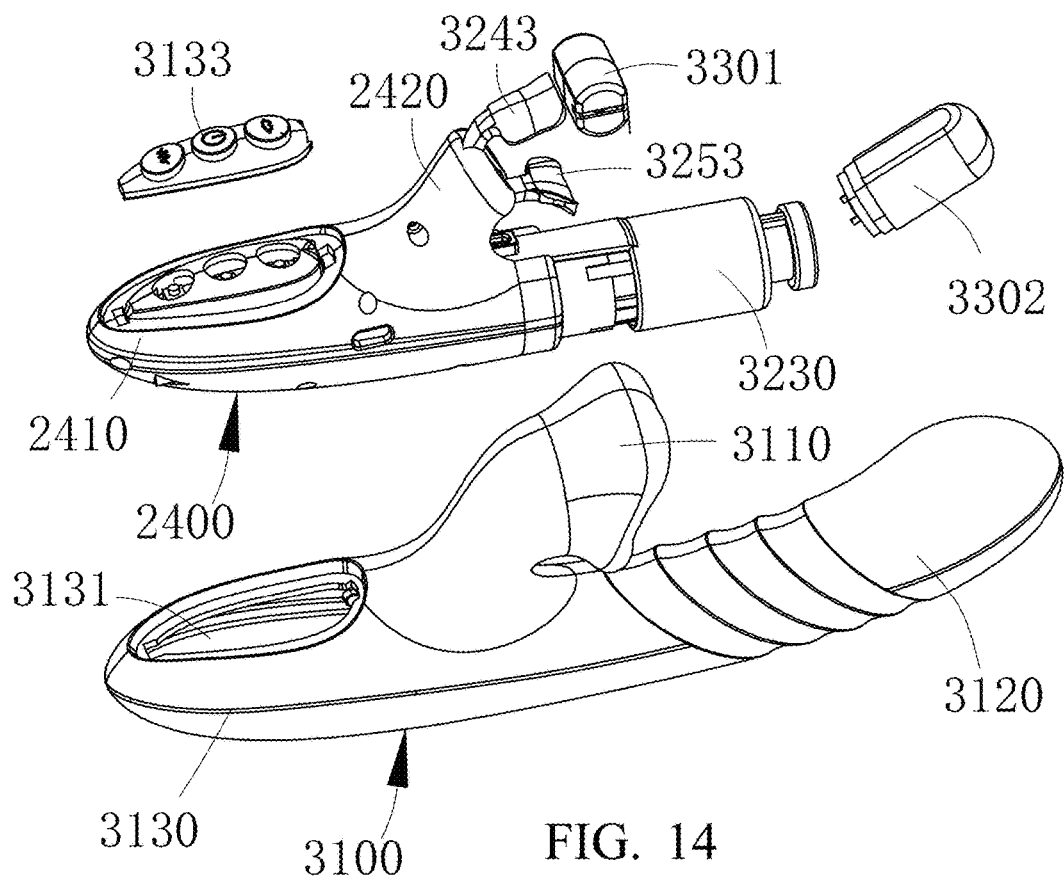
FIG. 14 is an exploded view of the massager shown in FIG. 12; and 14.
Figure 15:
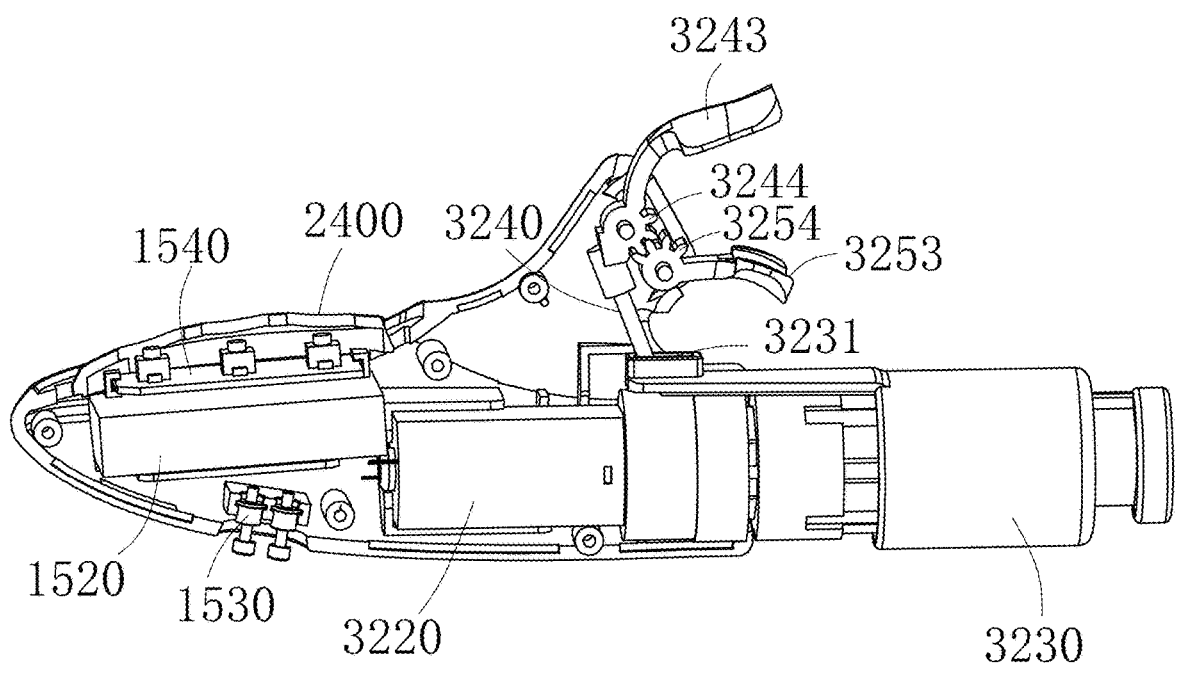
FIG. 15 is a view showing a driving mechanism of the massager shown in FIG.

Referring to FIGS. 13 to 15, the clamping part 3110, the positioning portion 3120 and the handle portion 3130 of the outer housing 3100 according to the third embodiment are all hollow. The inner housing 2400 of the massager 3000 includes a main body 2410 received in the handle portion 3130, and a branch portion 2420 connected at an angle to an end of the main body 2410 and received in the clamping part 3110. The main body 2410 is installed with a driving source 3220 of the driving mechanism 3200, a battery 1520, a first circuit board 1530 electrically connected to the battery 1520, and a second circuit board 1540 electrically connected to the driving source 3220 for controlling the driving source 3220. The second circuit board 1540 cooperates with a button portion 3133 which can be fixedly connected with the main body 2410 of the inner housing 2400, for example, by snapping with the main body 2410 of the inner housing 2400, and exposed to an opening 3131 of the handle portion 3130 of the outer housing 3100 for operation.

Preferably, in addition to the first vibration member 3301 received in the first accommodation chamber 3114 of the first engagement portion 3111 (instead of being received in the receiving sleeve 1246 of the first swing arm 1243 disclosed in the first embodiment), the massager 3000 according to the third embodiment further includes a second vibration member 3302 accommodated in the front end of the positioning portion 3120. The second vibration member 3302 is also preferably a vibration motor to perform vibration massage on the vagina or the rectum to improve the massage effect.

In this embodiment, the driving mechanism 3200 includes the driving source 3220, a movable sleeve 3230 connected to the driving source 3220, a swing component 3240 connected to the movable sleeve 3230, and the first swing arm 3243 and the second swing arm 3253. The driving source 3220 is configured to drive the movable sleeve 3230 to move back and forth. For example, the driving source 3220 can be a linear motor. The movable sleeve 3230 is installed in the chamber of the hollow positioning portion 3120, so that when the movable sleeve 3230 moves back and forth, the positioning portion 3120 (as stated above, the outer housing 3100 is made of a flexible material) will deform so that the free end of the positioning portion 3120 also moves back and forth to stimulate the vagina or rectum. Further, the outer surface of the movable sleeve 3230 has a slide groove 3231. In this embodiment, the swing component 3240 is configured as a rod, one end of which is movably received in the slide groove 3231, and the other end is connected to a first end of the first swing arm 3243. Preferably, a first gear 3244 is provided at the first end of the first swing arm 3243. It is also preferred that the swing component 3240, the first swing arm 3243 and the first gear 3244 are formed in one piece. A second gear 3254 is provided at a first end of the second swing arm 3253. The second gear 3254 meshes with the first gear 3244. Therefore, when the driving source 3220 drives the movable sleeve 3230 to move back and forth, the swing component 3240 will be driven to swing by the movable sleeve 3230, thereby driving the first swing arm 3243 and the second swing arm 3253 to swing, toward or away from each other simultaneously, respectively around centers of the first gear 3244 and the second gear 3254, so the first engagement portion 3111 and the second engagement portion 3112 will move toward or away from each other simultaneously, thereby achieving clamping massage.

In other embodiments, the driving mechanism 3200 may not include the second swing arm 3253 but the first swing arm 3243. That is, the second engagement portion 3112 can remain stationary, while the first engagement portion 3111 is driven by the first swing arm 3243 to move toward or away from the second engagement portion 3112, thereby achieving clamping massage.

While the disclosure has been particularly shown and described in conjunction with exemplary embodiments, it will be appreciated that variations and modifications will occur to those skilled in the art. The embodiments according to the present disclosure may be implemented in association with the formation and/or processing of structures illustrated and described herein as well as in association with other structures not illustrated. Moreover, in particular regard to the various functions performed by the above described components (assemblies, devices, circuits, etc.), the terms used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the disclosure. In addition, while a particular feature of the disclosure may have been disclosed with respect to only one of several embodiments, such feature may be combined with one or more features of the other embodiments as may be desired and advantageous for any given or particular application. Therefore, it is to be understood that the appended claims are intended to cover all such modifications and changes that fall within the true spirit of the disclosure.

The invention claimed is:

1. A massager, comprising:
a clamping part, comprising a first engagement portion and a second engagement portion which are opposite to each other and made of a flexible material, with a cavity defined between the first engagement portion and the second engagement portion;
a driving mechanism, comprising at least one swing arm which is disposed in at least one of the first engagement portion and the second engagement portion for driving the at least one of the first engagement portion and the second engagement portion to move toward or away from the other; and
a positioning portion which comprises at least one ring or an elongated stick;
wherein two ends of the first engagement portion are respectively connected to two ends of the second engagement portion to define two opposite connection portions, and the first engagement portion and the second engagement portion enclose the cavity.

2. The massager of claim 1, wherein each connection portion is V-shaped.

3. The massager of claim 1, wherein the clamping part further comprises a protrusion located in the cavity and between the first engagement portion and the second engagement portion, and the protrusion is made of a flexible material.

4. The massager of claim 3, wherein the massager further comprises at least one vibration member, and the at least one vibration member is disposed in at least one of the first engagement portion, the second engagement portion and the protrusion.

5. The massager of claim 1, wherein the positioning portion comprises at least one ring, a central axis of each ring is oriented parallel to a central axis of the cavity.

6. The massager of claim 5, wherein each ring has an inner diameter in a range of 5-100 mm.

7. The massager of claim 5, wherein the at least one ring comprises a first ring for surrounding a penis and a second ring for surrounding a pair of testicles.

8. The massager of claim 7, wherein the first ring has a first inner diameter, the second ring has a second inner diameter, and the first inner diameter is smaller than the second inner diameter.

9. The massager of claim 1, wherein the positioning portion comprises an elongated stick, and the elongated stick is configured to be inserted into a vagina or a rectum and has a length in a range of 2-30 cm.

10. The massager of claim 9, wherein the elongated stick is orientated at an angle to the clamping part.

11. The massager of claim 9, wherein the elongated stick comprises a front end and an opposing rear end, the clamping part is connected to the rear end of the elongated stick, and the massager further comprises a vibration member accommodated in the front end of the elongated stick.

12. The massager of claim 1, wherein the at least one swing arm consists of a first swing arm and a second swing arm, the first swing arm is disposed in the first engagement portion, the second swing arm is disposed in the second engagement portion, and the first swing arm and the second swing arm are configured to drive the first engagement portion and the second engagement portion to move toward or away from each other simultaneously.

13. The massager of claim 1, wherein the at least one swing arm consists of a first swing arm, the first swing arm is disposed in the first engagement portion, and the first swing arm is configured to drive the first engagement portion to move toward or away from the second engagement portion.

14. The massager of claim 1, wherein the driving mechanism further comprises an eccentric wheel, the at least one swing arm defines at least one slide groove, and the eccentric wheel is slidably received in the at least one slide groove for driving the at least one swing arm to swing.

15. The massager of claim 14, wherein the at least one swing arm consists of a first swing arm and a second swing arm, the first swing arm defines a first slide groove, and the second swing arm defines a second slide groove; and wherein the eccentric wheel comprises a first wheel and a second wheel eccentrically connected to the first wheel, the first and second wheels are slidably received in the first and second slide grooves respectively and configured to drive the first and second swing arms to swing toward or away from each other simultaneously.

16. The massager of claim 1, wherein the driving mechanism further comprises a swing component connected to the at least one swing arm and configured to drive the at least one swing arm to swing.

17. The massager of claim 16, wherein the at least one swing arm consists of a first swing arm and a second swing arm, the driving mechanism further comprises a first gear and a second gear respectively connected to the first swing arm and the second swing arm and meshed with each other, and the swing component is connected to the first gear and configured to drive the first swing arm and the second swing arm to swing toward or away from each other simultaneously.

18. The massager of claim 16, wherein the driving mechanism further comprises a movable sleeve, the movable sleeve defines a slide groove, one end of the swing component is movably received in the slide groove, and the movable sleeve is configured to move back and forth to drive the swing component to swing.

19. The massager of claim 18, wherein the elongated stick is made of a flexible material and has a chamber, and the movable sleeve is at least partially received in the chamber of the elongated stick so that when the movable sleeve moves back and forth to drive the swing component to swing, the elongated stick deforms so that a free end of the elongated stick also moves back and forth.

20. A massager, comprising:
   a clamping part, comprising a first engagement portion and a second engagement portion which are opposite to each other and made of a flexible material, with a cavity defined between the first engagement portion and the second engagement portion;
   a driving mechanism, comprising at least one swing arm which is disposed in at least one of the first engagement portion and the second engagement portion for driving the at least one of the first engagement portion and the second engagement portion to move toward or away from the other; and
   a positioning portion which comprises at least one ring or an elongated stick;
   wherein the driving mechanism further comprises an eccentric wheel, the at least one swing arm defines at least one slide groove, and the eccentric wheel is slidably received in the at least one slide groove for driving the at least one swing arm to swing.

* * * * *

UNITED STATES PATENT AND TRADEMARK OFFICE
CERTIFICATE OF CORRECTION

| | | |
|---|---|---|
| PATENT NO. | : 12,178,773 B1 | Page 1 of 1 |
| APPLICATION NO. | : 18/644172 | |
| DATED | : December 31, 2024 | |
| INVENTOR(S) | : Qinling Wang | |

It is certified that error appears in the above-identified patent and that said Letters Patent is hereby corrected as shown below:

On the Title Page

Column 1, The third Assignee's name should be corrected as below:
Junpeng Wu

Signed and Sealed this
Eleventh Day of February, 2025

Coke Morgan Stewart
*Acting Director of the United States Patent and Trademark Office*